United States Patent
Kladders

(10) Patent No.: US 8,528,548 B2
(45) Date of Patent: Sep. 10, 2013

(54) INHALER

(75) Inventor: Heinrich Kladders, Muelheim/Ruhr (DE)

(73) Assignee: Boehringer Ingelheim International GmbH, Ingelheim (DE)

(*) Notice: Subject to any disclaimer, the term of this patent is extended or adjusted under 35 U.S.C. 154(b) by 1110 days.

(21) Appl. No.: 12/441,177

(22) PCT Filed: Aug. 17, 2007

(86) PCT No.: PCT/EP2007/007268
§ 371 (c)(1),
(2), (4) Date: Jun. 17, 2009

(87) PCT Pub. No.: WO2008/034504
PCT Pub. Date: Mar. 27, 2008

(65) Prior Publication Data
US 2010/0051023 A1    Mar. 4, 2010

(30) Foreign Application Priority Data

Sep. 20, 2006 (DE) .................. 10 2006 044 756

(51) Int. Cl.
*A61M 16/00* (2006.01)
(52) U.S. Cl.
USPC ............................. 128/203.15; 128/203.19
(58) Field of Classification Search
USPC ........................ 128/203.15, 203.19
See application file for complete search history.

(56) References Cited

U.S. PATENT DOCUMENTS

| | | | |
|---|---|---|---|
| 5,653,227 A * | 8/1997 | Barnes et al. | 128/203.12 |
| 5,740,793 A | 4/1998 | Hodson et al. | |
| 6,012,454 A | 1/2000 | Hodson et al. | |
| 6,237,590 B1 * | 5/2001 | Leedom et al. | 128/203.15 |
| 2002/0088462 A1 * | 7/2002 | Genova et al. | 128/203.15 |
| 2006/0118107 A1 | 6/2006 | King | |
| 2007/0209661 A1 * | 9/2007 | Smyth et al. | 128/203.12 |

FOREIGN PATENT DOCUMENTS

| | | |
|---|---|---|
| GB | 2 279 273 A | 1/1995 |
| WO | 00/53248 A1 | 9/2000 |
| WO | 02/11894 A1 | 2/2002 |
| WO | 02/45783 A1 | 6/2002 |
| WO | 02/053215 A2 | 7/2002 |

OTHER PUBLICATIONS

International Search Report for PCT/EP2007/007268 mailed Apr. 15, 2008.

* cited by examiner

*Primary Examiner* — Lynne Anderson
(74) *Attorney, Agent, or Firm* — Michael P. Morris; David L. Kershner

(57) ABSTRACT

An inhaler (1) is proposed for inhaling a preparation (2) from a carrier (3) and/or through a delivery channel (16) as depicted in exemplary FIG. 1. The carrier or delivery channel is preferably flexible, flat, band-shaped, strip-shaped, thread-like, blister-like and/or film-like and can be set in vibration by a stream of air (5). The carrier or delivery channel is preferably set in vibration by a separate element (6), which for its part is set in motion or vibration by the stream of air. Alternatively, or in addition, the inhaler has a pump (10) with a telescopic pump chamber (20) for generating a stream of air for expelling and/or dispersing a preparation.

20 Claims, 2 Drawing Sheets

INHALER

This application is the national phase entry under 35 U.S.C. §371 of International Application No. PCT/EP2007/007268, filed Aug. 17, 2007, which claims priority to German Application No. 10 2006 044 756.5, filed Sep. 20, 2006, each of which is hereby incorporated by reference in its entirety.

The present invention relates to an inhaler according to the preamble of claim 1, 14 or 15 and a method of delivering and, in particular, atomising a preferably powdered formulation from a carrier.

The present invention relates in particular to an inhaler for the delivery or inhalation of a preferably powdered formulation, i.e. a powder inhaler. However, the formulation may theoretically also be in liquid phase, a dispersion or in some other fluidisable form.

The formulation is, in particular, a therapeutic agent or medicament. In particular, the formulation accordingly contains at least one active substance or consists thereof The formulation thus serves particularly for medical treatment or other therapeutic purposes.

In the present invention the formulation is contained in or by a carrier, particularly pre-dosed in individual doses.

EP 0 147 755 A2 discloses an inhaler for inhaling powdered medicaments from elongate capsules. The inhaler comprises a capsule chamber into which a capsule can be inserted manually. The capsule is pierced along its longitudinal side and thus opened by manual actuation of an opening device in the capsule chamber. During inhalation, an air current flowing through the capsule chamber causes the capsule to move back and forth in the capsule chamber, as a result of which the powdered medicament is expelled and dispersed in the air current.

The objective of the present invention is to provide a new inhaler and a new method to enable effective delivery and especially atomisation of an in particular powdered formulation by a simple method.

Figure 1:
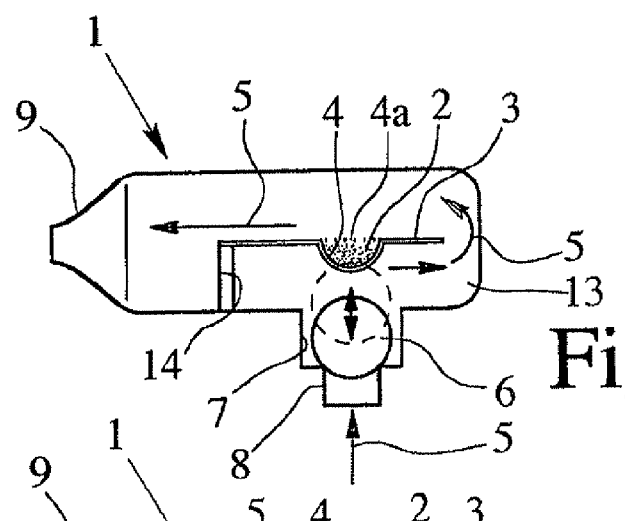

According to a first aspect of the present invention, a carrier or delivery channel for a formulation that is to be conveyed, provided and/or dispersed is of flexible, flat, ribbon-like, strip-like, thread-like, blister-like and/or film-like construction, while the carrier or delivery channel can be moved, for example set vibrating, by an air current in order to expel the formulation. In this way the formulation can be expelled, dispersed and/or discharged particularly effectively particularly from a corresponding receptacle in the carrier.

The formulation may be expelled using the air current for moving the carrier or delivery channel or using a different air current.

Another aspect of the present invention that can be implemented independently of the specific construction of the carrier or delivery channel is to provide an element which is separate from the carrier or delivery channel which is set in motion, more particularly set vibrating by the air current in order to move the carrier or delivery channel for the purpose of expelling, discharging or dispersing the formulation. For example, the element may be in the form of a ball or impact member.

In the present invention the terms "air" and "air current" are preferably also to be understood in the broader sense as encompassing a different gas or a current of such a gas. However, the term "air" is used throughout the following description as it is usually air that is used for driving or movement and/or as a conveying medium for conveying the formulation after it has been released from or by the carrier or for dispersing the formulation.

According to another aspect of the present invention which can also be implemented independently, the inhaler comprises a pump with a telescopically extendable pump chamber for producing an air current. This makes it possible in particular to produce a relative large air current or convey a large quantity per stroke of the pump and thereby achieve effective delivery and particularly atomisation of a preferably powdered formulation by a simple method. In the transporting state, the pump chamber can be pushed together so that the inhaler takes up very little space when being carried, for example in a pocket.

Individual aspects, features, properties and advantages of the present invention will become apparent from the claims and the following description of some preferred embodiments by reference to the drawings.

BRIEF DESCRIPTION OF THE DRAWINGS

FIG. 1 a schematic section through an inhaler according to a first embodiment;

FIG. 2 a schematic section through an inhaler according to a second embodiment;

FIG. 3 a schematic section through an inhaler according to a third embodiment;

FIG. 4 a schematic plan view of a carrier for an inhaler of the type proposed;

FIG. 5 a schematic section through an inhaler according to a fourth embodiment; and FIG. 6 a schematic section through an inhaler according to a fifth embodiment.

In the figures, the same reference numerals have been used for identical or similar parts, even if the associated description has been omitted. In particular, the same or corresponding advantages and properties are then obtained. For reasons of clarity or simplicity the individual figures are not to scale and have been reduced to the essential components relevant to the invention.

FIG. 1 diagrammatically shows the construction of a proposed inhaler 1 according to one embodiment. The inhaler 1 is preferably of portable design and/or operates purely mechanically, in particular.

The inhaler 1 serves for the delivery or inhalation of a preferably powdered formulation 2 in the sense described above. The formulation 2 is preferably pre-measured into a single dose or a number of doses which can preferably be dispensed one after the other and independently of one another.

In the embodiment shown, the formulation 2 is preferably pre-measured, i.e. pre-measured into an individual dose or a number of doses outside the inhaler 1. However, it is theoretically also possible for the formulation 2 to be measured out just before each inhalation and/or in the inhaler 1.

A carrier 3 carries the formulation 2 or holds it in readiness. In particular, the carrier 3 has at least one recess or receptacle 4 or the like for receiving in particular one dose of the formulation 2. However, other design solutions are also possible. For example, the formulation 2 may be arranged or distributed over the surface or over part of the surface or over the entire surface of the carrier 3. Other configurations are also possible here. In particular, the carrier 3 may also be constructed as a container, chamber, sleeve or the like.

In the first embodiment the carrier 3 is particularly flexible, flat, in the form of a ribbon, strip, blister and/or foil. It is made from a suitable material, particularly plastics, metal foil, a composite material or the like.

The carrier 3 may have only one receptacle 4 or a number of receptacles 4. Each receptacle 4 may if necessary be covered by an optional cover 4a, as indicated by way of example in FIG. 1. In order to expel the formulation 2 the cover 4a can then preferably be opened, torn off or the like. For example, the cover 4a may be cut open, torn off, perforated or in some other way at least partially removed and/or opened to allow the formulation 2 to be expelled. Particularly preferably, the opening may also be carried out by movement of the carrier 3, as will be described in more detail hereinafter. The cover 4a and/or a relatively small exit opening or the like particularly preferably causes the formulation 2 to be dispensed and expelled comparatively slowly, particularly at a desired rate.

The carrier 3 can be moved, particularly set vibrating, by means of an air current 5 in order to expel the formulation 2, i.e. to release the formulation 2 from the carrier 3 or from the receptacle 4. The air current 5 may act on or move the carrier 3 directly and/or indirectly.

In the first embodiment the air current 5 acts in particular indirectly on the carrier 3. For this purpose the inhaler 1 has an element 6 which is separate from the carrier 3 and which is moveable by the air current 5 in order to move the carrier 3. In particular, the element 6 can be set vibrating by the air current 5.

In the embodiment shown, the element 6 is preferably substantially spherical in design. However, it may also have any other suitable shape, for example an elongate, oval or rotationally symmetrical shape.

Preferably the element 6 is accommodated in a chamber 7. The air current 5 can be fed into the chamber 7 through a supply channel 8. The supply channel 8 opens into the chamber 7 in particular with a cross section which is reduced by comparison with the chamber 7 and particularly by comparison with the element 6. However, other arrangements are also possible.

Being of suitable dimensions and suitably arranged, the element 6 is moved back and forth by the air current 5 and particularly set vibrating, most preferably along the main direction of flow. Particularly preferably the geometric conditions correspond to the data in EP 0147755 A2, which is cited as a supplementary disclosure on this subject.

In particular, the back and forth movement of the element 6 is brought about by the so called Bernoulli effect.

The element 6 hits the carrier 3 particularly at right angles to the longitudinal or surface direction, most preferably on the carrier side remote from the formulation 2. The carrier 2 is then set in a preferably flattering or wave-like motion or vibration by the movement of the element 6. This very effectively produces the desired movement of the carrier 3 in order to assist or achieve the dispersal and release of the formulation 2 from the carrier 3 or from an associated receptacle 4 or the like. In addition, the carrier 3 or the receptacle 4 may be opened, e.g. torn open, by the movement.

Particularly preferably the element 6 strikes the carrier 3. In this case the element 6 forms an impact member. However, other operating mechanisms may come into play.

Preferably, the air flow 5 also forms a conveying medium for dispersing and/or conveying the formulation 2 which has been released from the carrier 3, particularly by the movement thereof, and preferably to expel it through a mouthpiece 9 of the inhaler 1 and dispense it to a user (not shown). However, another or separate air current or other air in the sense mentioned previously, i.e. other gas, may also be used as the conveying medium for the formulations 2.

In the first embodiment the airflow 5 is preferably generated by the inhaling or breathing in of the user (not shown), particularly by the intake of ambient air. The air current 5 first of all moves the element 6 and is then preferably guided onto the other flat side of the carrier 3 in order to disperse or further transport the formulation 2 which has preferably already been loosened by the movement of the carrier 3 and expel it through the mouthpiece 9.

Theoretically, the carrier 3 may also be flexible, flat, in the shape of a ribbon, strip, blister and/or foil. Alternatively or additionally, the carrier 3 may also take the form of a chamber, capsule, hollow body, a cylinder or a sphere.

Figure 2:
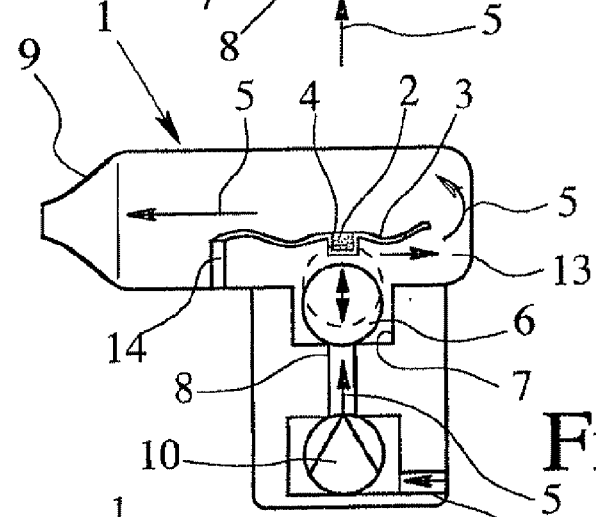

FIG. 2 shows, in a diagrammatic section corresponding to FIG. 1, a second embodiment of the proposed atomiser 1. The second embodiment corresponds at least substantially to the first embodiment, with the result that the following description will discuss only the major differences between this and the first embodiment. The remarks and explanations appearing previously continue to apply in a supplementary or corresponding manner.

In the second embodiment the atomiser 1 has a pump 10 for producing the air current 5. In the embodiment shown, ambient air is taken in by the pump 10. However, as already explained previously, other gas may also be used. The term "air" should therefore preferably be taken in a correspondingly broad sense.

In the embodiment shown the pump 10 is preferably manually operable or driveable. However, the pump 10 may also be driven by different means, for example electrically. The pump 10 may for example be switched on after being triggered by breathing, so that as the user inhales or breathes in, the pump 10 is automatically started up, for example as the result of a reduced pressure, airflow or the like generated as the user first breathes in.

The pump 10 may also be understood in general terms as being a device for producing and/or preparing pressurised air or other gas. Accordingly, it may for example be a compressed air or gas container or the like, preferably with a corresponding valve device. Alternatively, the air current may also be generated or prepared by some other means.

In the first and second embodiment the carrier 3 preferably forms a limitation for the element 6 in the chamber 7 and/or covers the chamber 7 to a greater or lesser extent. However it is theoretically also possible to use for this purpose an additional guide, holder, limit or the like, particularly to restrict the room for movement of the element 6 and/or its guide.

Figure 3:
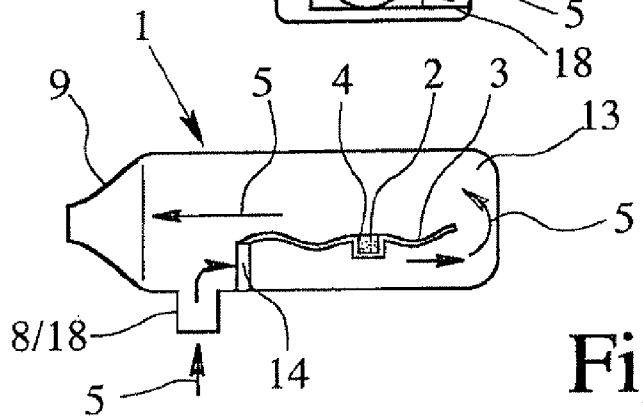

FIG. 3 shows a third embodiment of the proposed inhaler 1. Only major differences from the first two embodiments will be described hereinafter, which means that the remarks and explanations provided earlier continue to apply accordingly or in a supplementary capacity.

In the third embodiment the airflow 5 preferably sets the carrier 3 directly in motion, particularly in vibration. Vibration occurs in particular at least substantially or with a substantial component at right angles to the longitudinal or surface direction of the carrier 3.

In particular, the air current 5 is guided over a flat side at least substantially parallel to the flat side of the carrier 3 and/or to a free end of the carrier 3.

In the third embodiment the air current 5 is preferably in turn used as a conveying medium for expelling the formulation 2 through the mouthpiece 9. The air current 5 is generated in particular by a user (not shown) inhaling or breathing in. However, it is possible if necessary to use the pump 10 as in the second embodiment in order to generate and/or assist the air current 5.

Generally it should be pointed out that the pump 10 may also be used only to produce the air current 5 for setting the carrier 3 in motion. The conveying medium or another air current can then serve to disperse and deliver the formulation 2 and may be produced for example by the breathing in or inhalation.

Figure 4:
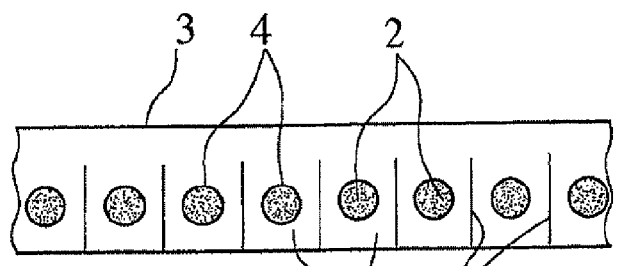

FIG. 4 shows in a schematic plan view a preferred embodiment of the carrier 3. The carrier 3 is in particular endless or in the shape of a ribbon or strip, in particular, and is of flexible and/or at least substantially flat or planar construction, in particular.

The carrier 3 may be produced from foil and/or composite material, for example, and/or in the form of a blister.

In the embodiment shown the carrier 3 preferably has several receptacles 4, in particular arranged in a row, each preferably containing one dose of the formulation 2.

Each receptacle 4 or dose of formulation 2 is preferably arranged on a separate portion 11 of the carrier 3. The portions 11 are shaped like tongues, for example, or are separated from one another by cuts 12 or in some other way, so that the sections 11 can move independently of one another, in particular, at right angles to the surface direction. This assists the movement of the carrier 3 or the respective section 11 for dispensing the formulation 2 in the inhaler 1.

The carrier 3 can preferably be moved stepwise through the inhaler 1 or through or into a chamber 13 in the inhaler 1 or the like, in order to set a receptacle 4 or dose of the formulation 2 or a section 11 in the chamber 13 in motion by means of the air current 5 in the desired manner and thereby disperse and expel the formulation 2. The sections 11 or receptacles 4 are then moved individually, one after the other, by the air current 5, so that the individual doses of the formulation 2 can be delivered singly, as desired.

However, it is theoretically also possible to deliver a number of doses and/or different formulations to, if necessary from different receptacles 4, at the same time. For this, the carrier 3 may for example have a plurality of receptacles 4 possibly containing different formulation 2 on one section 11. However, other configurations are also possible.

In the example shown, the formulation 2 is preferably pre-measured into the individual receptacles 4 and hermetically sealed, in particular for storage. The opening of the individual receptacles 4 or the tearing open of the carrier 3 or the like then preferably takes place immediately before or during the inhalation. If necessary the opening may be carried out by means of an opening device (not shown) and/or by the movement of the carrier 3, optionally by the impact of the element 6. If necessary the element 6 may be provided for this purpose with corresponding opening elements, cutters, projections or the like.

According to an alternative embodiment not shown here, it is possible to provide the carrier 3 with the formulation 2, for example fill a receptacle 4, only directly before or during the transportation into the inhaler 1 or the chamber 13.

According to another alternative embodiment it is also possible to make the surface of the carrier 3 relatively rough so that it picks up the preferably powdered formulation 2 on its surface and suitably releases it again as it moves as a result of the air current 5 or the element 6, in particular so that the formulation 2 is dispersed into a gaseous conveying medium and expelled in the desired manner. For example, the carrier 3 may be of a thread-like construction and may be conveyed or pulled through a reservoir (not shown) containing the formulation 2 in order to pick up the formulation 2. According to another alternative embodiment, the carrier 3 may also be a porous or fleece-like, textile-like or carpet-like material having an in particular correspondingly rough and/or open pored or open surface.

In the embodiments shown in FIGS. 1 to 3 the carrier 3 is preferably held or guided by a suitable, schematically shown guide device 14 in the chamber 13, particularly preferably only at one side, edge, corner or end. In the third embodiment, particularly on the side from which the air flow 5 flows in or arrives (FIG. 3, left hand side).

Generally, an inhaler 1 is proposed in particular for inhaling a formulation 2 from the carrier 3 or from receptacles 4, each of which contains one dose of the formulation 2.

The receptacles 4 are preferably each emptied by being set in motion directly by an incoming current of gas or air 5 or by the element 6 which is moved thereby. The current of gas or air may be produced by the user or patient breathing in and/or actively by the inhaler 1. For ease of operation, the inhaler 1 in particular comprises a device for automatic filling, emptying and/or cleaning, in particular.

The dispersing process, preferably provided (movement of the carrier 3 or the opened or opening receptacle 4 in the current of gas or air 5 for expelling and dispersing the formulation 2 in the gas or air current 5) has various advantages. It permits very uniform dispersion with good disaggregation of the particles. It allows relative independence on the flow rate. In particular the expulsion movement or vibration or oscillation and hence the delivery of the formulation 2 only begins when a flow rate of 10 or 20 litres per minute is reached. Moreover, an acoustic signal which is perceptible to the user may be produced by the expulsion movement, i.e. during inhalation.

With regard to the embodiments of the inhaler 1 described previously and hereinafter it should be noted that the carrier 3 preferably forms or defines a channel-shaped chamber 13, particularly at least partially or on one side, while the carrier 3 or chamber 13 has the air current 5 flowing through and/or around it. However, theoretically, other configurations are also possible.

Figure 5:
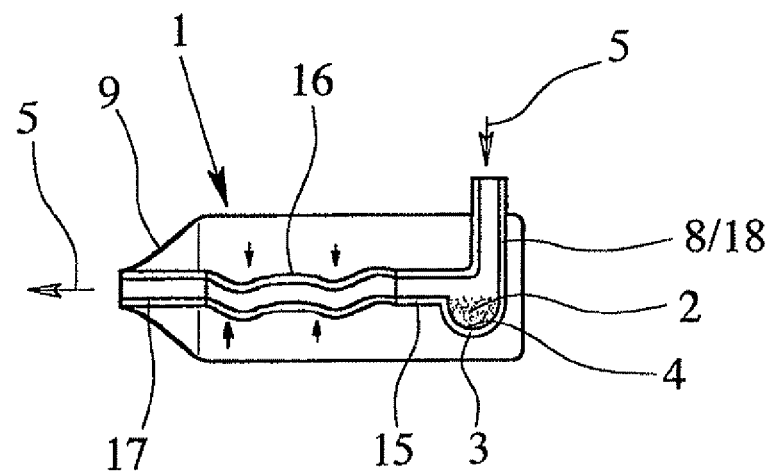

FIG. 5 shows in diagrammatic section a fourth embodiment of the proposed inhaler 1. The fourth embodiment is basically very similar to the third embodiment, which means that the explanations and comments made regarding the latter still apply accordingly or in a supplementary capacity.

In the fourth embodiment a delivery channel 16 which is flexible and/or movable at least in parts or on one side is adjacent to the carrier 3 or the receptacle 4 or some other reservoir for the formulation 2, said delivery channel particularly preferably being attached to the carrier 3 or the receptacle 4, the other reservoir for the formulation 2 or the like, via an in particular rigid connecting portion 15.

At the outlet end the delivery channel 16 is preferably connected to the mouthpiece 9, in this embodiment via a preferably rigid dispensing channel 17 or the like.

In the embodiment shown the delivery channel 16 is preferably tubular and/or flat in cross-section.

In particular, the delivery channel 16 or its wall is formed by flexible, preferably textile-like or foil-like material, at least in part, on one side or completely.

In contrast to the other embodiments, movement of the carrier 3 or the receptacle 4 is still theoretically possible here but is not necessary. In particular, the carrier 3 or the receptacle 4 or some other reservoir for the formulation 2 may be of rigid or immovable design, but optionally replaceable, as is preferably the case in the embodiment shown.

The air current 5 which is sucked in particularly as the user breathes in or inhales through the supply channel 8 or an inlet channel 18 causes the preferably powdered formulation 2 to be released or conveyed from the carrier 3 or from the receptacle 4 through the delivery channel 16 to the mouthpiece 9.

The air current 5 ensures that the delivery channel 16 or its wall is moved at least on one side or in parts, particularly by the Bernoulli effect. In the embodiment shown, there is a fluttering and/or wavelike movement, in particular, and/or an alternating radial expansion and contraction or pulling together of the delivery channel 16. This movement of the delivery channel 16 may bring about a substantial improvement in the dispersing of the formulation 2 in the air current 5 or in some other conveying medium. Alternatively or additionally, different formulations 2 may also be effectively mixed or combined in this manner.

In the embodiment shown the air current 5 flows through the delivery channel 16. However, the air current 5 may alternatively or additionally flow around the delivery channel 16 or flow over it in some other way.

Instead of a direct movement of the delivery channel 16 produced by the air current 5 or its effects, this may be carried out indirectly, for example again by means of the element 6 which is moved by the air current 5. In this respect reference is made to the other embodiments.

If required, the air current 5 may also be used only to move the channel section 16 and a separate air current or a separate conveying medium may be used to convey the formulation 2 and expel it.

It should be noted that the term "delivery channel" is preferably to be interpreted very broadly. For example, the delivery channel 16 may be bounded on one side by a rigid wall and on another side may be bounded by a flexible and/or movable wall or the like, the delivery channel 16 being formed therebetween. Moreover, any desired cross-sectional configurations are possible. The delivery channel 16 is preferably of elongate construction and comprises in particular a relatively small cross-section or diameter in relation to its length, but other configurations and geometries are possible here too. For example, the delivery channel 16 may be very short in design and/or may be larger in diameter than in length.

Figure 6:
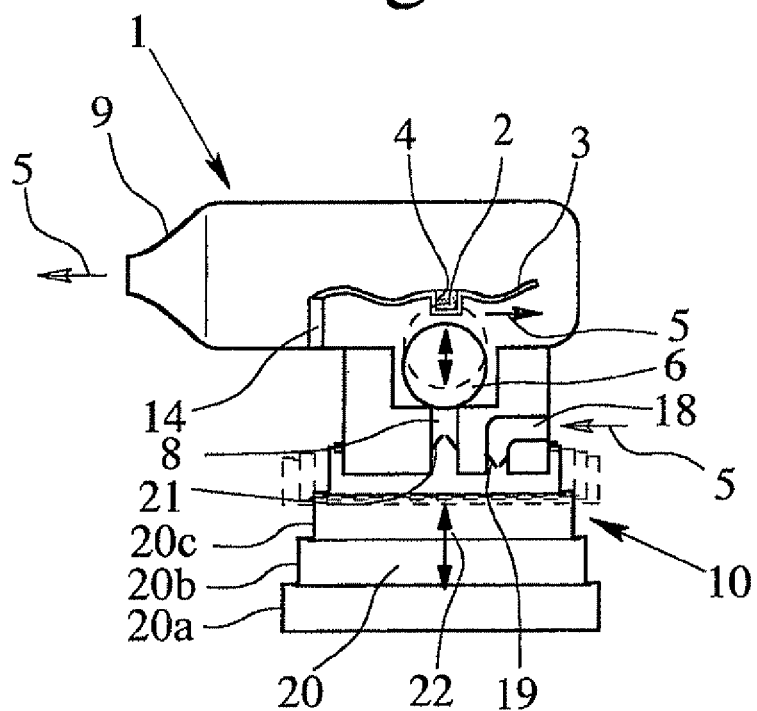

FIG. 6 shows a fifth embodiment of the proposed inhaler 2. The fifth embodiment is very similar to the second embodiment, and consequently the remarks and explanations relating to the latter apply here correspondingly or in a supplementary capacity.

In the fifth embodiment the pump 10 is most preferably designed for conveying air or generating the air current 5.

The pump preferably has an associated inlet channel 18 for sucking in an ambient air. However, other design solutions are also possible.

The pump 10 preferably has an inlet valve 19, a pump chamber 20 and/or an outlet valve 21.

The pump chamber 20 is preferably telescopic, in particular can be extended or collapsed telescopically, as indicated by the double arrow 22 in FIG. 6.

During telescopic movement or pumping, ambient air is taken in alternately through the inlet channel 18 and the optional inlet valve 19 and expelled through the outlet valve 21 and the feed channel 8. The air is thus placed under pressure in order to generate the air current 5, particularly so as to expel the formulation 2 and/or bring about a movement of the carrier 3, the element and/or the channel section 16, as already described hereinbefore.

The pump 10 preferably has the largest possible pump volume while retaining a compact structure. Thanks to the telescopic nature of the pump chamber 20 a comparatively large pumping volume can be achieved in order to obtain a powerful air current 5 and thereby ensure effective expulsion or dispersion of the formulation 2. In the transporting state the pump chamber 20 can be collapsed so that the inhaler 1 takes up very little room while being carried, for example in a pocket.

Preferably, the pump chamber 20 comprises in particular external and/or annular wall or housing sections 20a, 20b and 20c. In particular the pump chamber 20 is bounded or formed by at least two, three or more housing parts 20a, 20b, 20c. Particularly preferably, the wall portions 20a, 20b, 20c form outer housing parts of the inhaler 1.

The wall portions 20a, 20b, 20c can preferably be pushed axially into one another or pulled axially apart from one another. FIG. 6 shows the extended position. The collapsed state of the inhaler 1 or pump chamber 20 or wall portions 20a, 20b, 20c is shown by dotted lines.

Particularly preferably, the outermost and/or lowest or end wall portion 20a is constructed in the manner of a pot or as an end piece or handle for a user (not shown).

Particularly preferably, the pump chamber 20 can be locked in the collapsed state by latching or other means, for example for transportation purposes.

Particularly preferably, the pump volume of the pump chamber 20 is selected or adapted such that on each stroke of the pump a sufficient quantity of air is pumped or made available to allow total expulsion of a dose of the formulation 2 or total inhalation.

The pump chamber 20 in the embodiment shown is preferably made up of a number of, in particular, rigid wall portions 20a, 20b, 20c. The wall of the pump chamber 20 is correspondingly telescopic. Alternatively or additionally the pump chamber 20 may be of a concertina-like design or may be made up of a flexible wall. The remarks and explanations provided hereinbefore will then apply accordingly. In particular, the "concertina-like" design is preferably also understood as being "telescopic" for the purposes of the present invention.

The pump 10 or telescopic pump chamber 20 described hereinbefore can be used independently of the embodiments described, in particular in other inhalers 1, atomisers, dispensers or the like.

In the embodiment shown the inhaler preferably operates purely mechanically. However, it is theoretically also possible for the inhaler 1 to operate electrically or electronically and/or to comprise such components or parts. This applies particularly to a trigger device for initiating the release of the formulation 2 or for fixing the inhalation time, a drive, a pump, a counter, a lock, a control device or the like.

Individual features and aspects of the different embodiments may also be combined with one another as desired or used in other designs of inhalers.

The present invention is not restricted to inhalers but may also be used accordingly in other atomisers. Therefore, the term "inhaler" is preferably to be taken in a wider sense as meaning that it also encompasses other types of dispensers or atomisers, particularly for medical or other therapeutic purposes.

Some preferred ingredients and/or compositions of the preferably medical formulation 2 are listed below. As already mentioned they consists in particular of powders, or fluids in the broadest sense. Most preferably, the formulation 2 contains:

The compounds listed below may be used in the device according to the invention on their own or in combination. In the compounds mentioned below, W is a pharmacologically active substance and is selected (for example) from among the betamimetics, anticholinergics, corticosteroids, PDE4-inhibitors, LTD4-antagonists, EGFR-inhibitors, dopamine agonists, H1-antihistamines, PAF-antagonists and PI3-kinase inhibitors. Moreover, double or triple combinations of W may be combined and used in the device according to the invention. Combinations of W might be, for example:

W denotes a betamimetic, combined with an anticholinergic, corticosteroid, PDE4-inhibitor, EGFR-inhibitor or LTD4-antagonist, W denotes an anticholinergic, combined with a betamimetic, corticosteroid, PDE4-inhibitor, EGFR-inhibitor or LTD4-antagonist, W denotes a corticosteroid, combined with a PDE4-inhibitor, EGFR-inhibitor or LTD4-antagonist W denotes a PDE4-inhibitor, combined with an EGFR-inhibitor or LTD4-antagonist W denotes an EGFR-inhibitor, combined with an LTD4-antagonist.

The compounds used as betamimetics are preferably compounds selected from among albuterol, arformoterol, bambuterol, bitolterol, broxaterol, carbuterol, clenbuterol, fenoterol, formoterol, hexoprenaline, ibuterol, isoetharine, isoprenaline, levosalbutamol, mabuterol, meluadrine, metaproterenol, orciprenaline, pirbuterol, procaterol, reproterol, rimiterol, ritodrine, salmefamol, salmeterol, soterenol, sulphonterol, terbutaline, tiaramide, tolubuterol, zinterol, CHF-1035, HOKU-81, KUL-1248 and 3-(4-{6-[2-hydroxy-2-(4-hydroxy-3-hydroxymethyl-phenyl)-ethylamino]-hexyloxy}-butyl)-benzyl-aulphonamide 5-[2-(5,6-diethyl-indan-2-ylamino)-1-hydroxy-ethyl]-8-hydroxy-1H-quinolin-2-one 4-hydroxy-7-[2-{[2-{[3-(2-phenylethoxy)propyl]sulphonyl}ethyl]-amino}ethyl]-2(3H)-benzothiazolone 1-(2-fluoro-4-hydroxyphenyl)-2-[4-(1-benzimidazolyl)-2-methyl-2-butylamino]ethanol 1-[3-(4-methoxybenzyl-amino)-4-hydroxyphenyl]-2-[4-(1-benzimidazolyl)-2-methyl-2-butylamino]ethanol 1-[2H-5-hydroxy-3-oxo-4H-1,4-benzoxazin-8-yl]-2-[3-(4-N,N-dimethylaminophenyl)-2-methyl-2-propylamino]ethanol 1-[2H-5-hydroxy-3-oxo-4H-1,4-benzoxazin-8-yl]-2-[3-(4-methoxyphenyl)-2-methyl-2-propylamino]ethanol 1-[2H-5-hydroxy-3-oxo-4H-1,4-benzoxazin-8-yl]-2-[3-(4-n-butyloxyphenyl)-2-methyl-2-propylamino]ethanol 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol 5-hydroxy-8-(1-hydroxy-2-isopropylaminobutyl)-2H-1,4-benzoxazin-3-(4H)-one 1-(4-amino-3-chloro-5-trifluoromethylphenyl)-2-tert.-butylamino)ethanol 6-hydroxy-8-{1-hydroxy-2-[2-(4-methoxy-phenyl)-1,1-dimethyl-ethylamino]-ethyl}-4H-benzo[1,4]oxazin-3-one 6-hydroxy-8-{1-hydroxy-2-[2-(ethyl 4-phenoxy-acetate)-1,1-dimethyl-ethylamino]-ethyl}-4H-benzo[1,4]oxazin-3-one 6-hydroxy-8-{1-hydroxy-2-[2-(4-phenoxy-acetic acid)-1,1-dimethyl-ethylamino]-ethyl}-4H-benzo[1,4]oxazin-3-one 8-{2-[1,1-dimethyl-2-(2,4,6-trimethylphenyl)-ethylamino]-1-hydroxy-ethyl}-6-hydroxy-4H-benzo[1,4]oxazin-3-one 6-hydroxy-8-{1-hydroxy-2-[2-(4-hydroxy-phenyl)-1,1-dimethyl-ethylamino]-ethyl}-4H-benzo[1,4]oxazin-3-one 6-hydroxy-8-{1-hydroxy-2-[2-(4-isopropyl-phenyl)-1,1 dimethyl-ethylamino]-ethyl}-4H-benzo[1,4]oxazin-3-one 8-{2-[2-(4-ethyl-phenyl)-1,1-dimethyl-ethylamino]-1-hydroxy-ethyl}-6-hydroxy-4H-benzo[1,4]oxazin-3-one 8-{2-[2-(4-ethoxy-phenyl)-1,1-dimethyl-ethylamino]-1-hydroxy-ethyl}-6-hydroxy-4H-benzo[1,4]oxazin-3-one 4-(4-{2-[2-hydroxy-2-(6-hydroxy-3-oxo-3,4-dihydro-2H-benzo[1,4]oxazin-8-yl)-ethylamino]-2-methyl-propyl}-phenoxy)-butyric acid 8-{2-[2-(3,4-difluoro-phenyl)-1,1-dimethyl-ethylamino]-1-hydroxy-ethyl}-6-hydroxy-4H-benzo[1,4]oxazin-3-one 1-(4-ethoxy-carbonylamino-3-cyano-5-fluorophenyl)-2-(tert-butylamino)ethanol 2-hydroxy-5-(1-hydroxy-2-{2-[4-(2-hydroxy-2-phenyl-ethylamino)-phenyl]-ethylamino}-ethyl)-benzaldehyde N-[2-hydroxy-5-(1-hydroxy-2-{2-[4-(2-hydroxy-2-phenyl-ethylamino)-phenyl]-ethylamino}-ethyl)-phenyl]-formamide 8-hydroxy-5-(1-hydroxy-2-{2-[4-(6-methoxy-biphenyl-3-ylamino)-phenyl]-ethylamino}-ethyl)-1H-quinolin-2-one 8-hydroxy-5-[1-hydroxy-2-(6-phenethylamino-hexylamino)-ethyl]-1H-quinolin-2-one 5-[2-(2-{4-[4-(2-amino-2-methyl-propoxy)-phenylamino]-phenyl}-ethylamino)-1-hydroxy-ethyl]-8-hydroxy-1H-quinolin-2-one

[3-(4-{6-[2-hydroxy-2-(4-hydroxy-3-hydroxymethyl-phenyl)-ethylamino]-hexyloxy}-butyl)-5-methyl-phenyl]-urea 4-(2-{6-[2-(2,6-dichloro-benzyloxy)-ethoxy]-hexylamino}-1-hydroxy-ethyl)-2-hydroxymethyl-phenol 3-(4-{6-[2-hydroxy-2-(4-hydroxy-3-hydroxymethyl-phenyl)-ethylamino]-hexyloxy}-butyl)-benzylsulphonamide 3-(3-{7-[2-hydroxy-2-(4-hydroxy-3-hydroxymethyl-phenyl)-ethylamino]-heptyloxy}-propyl)-benzylsulphonamide 4-(2-{6-[4-(3-cyclopentanesulphonyl-phenyl)-butoxy]-hexylamino}-1-hydroxy-ethyl)-2-hydroxymethyl-phenol N-adamantan-2-yl-2-(3-{2-[2-hydroxy-2-(4-hydroxy-3-hydroxymethyl-phenyl)-ethylamino]-propyl}-phenyl)-acetamide optionally in the form of the racemates, enantiomers, diastereomers thereof and optionally in the form of the pharmacologically acceptable acid addition salts, solvates or hydrates thereof. According to the invention the acid addition salts of the betamimetics are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The anticholinergics used are preferably compounds selected from among the tiotropium salts, preferably the bromide salt, oxitropium salts, preferably the bromide salt, flutropium salts, preferably the bromide salt, ipratropium salts, preferably the bromide salt, glycopyrronium salts, preferably the bromide salt, trospium salts, preferably the chloride salt, tolterodine. In the above-mentioned salts the cations are the pharmacologically active constituents. As anions the above-mentioned salts may preferably contain the chloride, bromide, iodide, sulphate, phosphate, methanesulphonate, nitrate, maleate, acetate, citrate, fumarate, tartrate, oxalate, succinate, benzoate or p-toluenesulphonate, while chloride, bromide, iodide, sulphate, methanesulphonate or p-toluenesulphonate are preferred as counter-ions. Of all the salts the chlorides, bromides, iodides and methanesulphonates are particularly preferred.

Other preferred anticholinergics are selected from among the salts of formula AC-1

AC-1

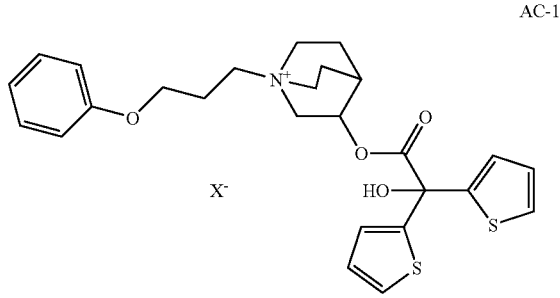 [SMILES: O=C(OC1C[N+]2(CCCOc3ccccc3)CCC1CC2)C(O)(c1cccs1)c1cccs1 ; "X-"]

AC-2-base

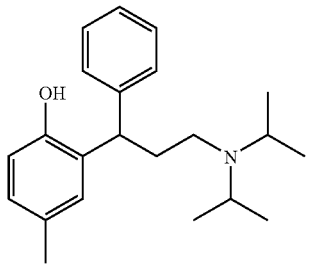

wherein X⁻ denotes an anion with a single negative charge, preferably an anion selected from among the fluoride, chloride, bromide, iodide, sulphate, phosphate, methanesulphonate, nitrate, maleate, acetate, citrate, fumarate, tartrate, oxalate, succinate, benzoate and p-toluenesulphonate, preferably an anion with a single negative charge, particularly preferably an anion selected from among the fluoride, chloride, bromide, methanesulphonate and p-toluenesulphonate, particularly preferably bromide, optionally in the form of the racemates, enantiomers or hydrates thereof. Of particular importance are those pharmaceutical combinations which contain the enantiomers of formula AC-1-en AC-1-en

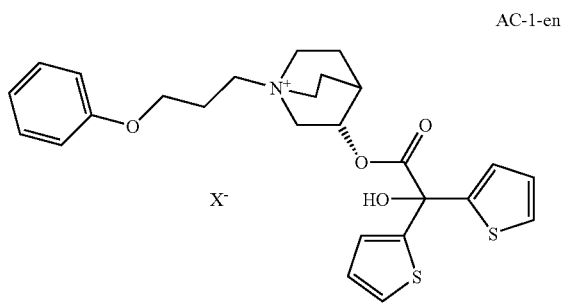

wherein X⁻ may have the above-mentioned meanings. Other preferred anticholinergics are selected from the salts of formula AC-2

AC-2

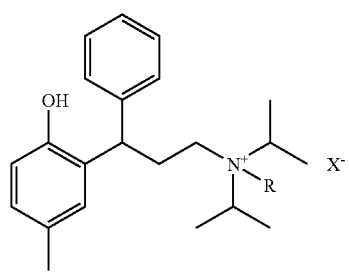

wherein R denotes either methyl or ethyl and wherein X⁻ may have the above-mentioned meanings. In an alternative embodiment the compound of formula AC-2 may also be present in the form of the free base AC-2-base.

Other specified compounds are:
tropenol 2,2-diphenylpropionate methobromide,
scopine 2,2-diphenylpropionate methobromide,
scopine 2-fluoro-2,2-diphenylacetate methobromide,
tropenol 2-fluoro-2,2-diphenylacetate methobromide;
tropenol 3,3',4,4'-tetrafluorobenzilate methobromide,
scopine 3,3',4,4'-tetrafluorobenzilate methobromide,
tropenol 4,4'-difluorobenzilate methobromide,
scopine 4,4'-difluorobenzilate methobromide,
tropenol 3,3'-difluorobenzilate methobromide,
scopine 3,3'-difluorobenzilate methobromide;
tropenol 9-hydroxy-fluorene-9-carboxylate methobromide;
tropenol 9-fluoro-fluorene-9-carboxylate methobromide;
scopine 9-hydroxy-fluorene-9-carboxylate methobromide;
scopine 9-fluoro-fluorene-9-carboxylate methobromide;
tropenol 9-methyl-fluorene-9-carboxylate methobromide;
scopine 9-methyl-fluorene-9-carboxylate methobromide;
cyclopropyltropine benzilate methobromide;
cyclopropyltropine 2,2-diphenylpropionate methobromide;
cyclopropyltropine 9-hydroxy-xanthene-9-carboxylate methobromide;
cyclopropyltropine 9-methyl-fluorene-9-carboxylate methobromide;
cyclopropyltropine 9-methyl-xanthene-9-carboxylate methobromide;
cyclopropyltropine 9-hydroxy-fluorene-9-carboxylate methobromide;
cyclopropyltropine methyl 4,4'-difluorobenzilate methobromide.
tropenol 9-hydroxy-xanthene-9-carboxylate methobromide;
scopine 9-hydroxy-xanthene-9-carboxylate methobromide;
tropenol 9-methyl-xanthene-9-carboxylate methobromide;
scopine 9-methyl-xanthene-9-carboxylate methobromide;
tropenol 9-ethyl-xanthene-9-carboxylate methobromide;
tropenol 9-difluoromethyl-xanthene-9-carboxylate methobromide;
scopine 9-hydroxymethyl-xanthene-9-carboxylate methobromide, The above-mentioned compounds may also be used as salts within the scope of the present invention, wherein instead of the methobromide the salts metho-X are used, wherein X may have the meanings given hereinbefore for X⁻.

As corticosteroids it is preferable to use compounds selected from among beclomethasone, betamethasone, budesonide, butixocort, ciclesonide, deflazacort, dexamethasone, etiprednol, flunisolide, fluticasone, loteprednol, mometasone, prednisolone, prednisone, rofleponide, triamcinolone, RPR-106541, NS-126, ST-26 and
(S)-fluoromethyl 6,9-difluoro-17-[(2-furanylcarbonyl)oxy]-11-hydroxy-16-methyl-3-oxo-androsta-1,4-diene-17-carbothionate
(S)-(2-oxo-tetrahydro-furan-3S-yl)6,9-difluoro-11-hydroxy-16-methyl-3-oxo-17-propionyloxy-androsta-1,4-diene-17-carbothionate, cyanomethyl 6α,9α-difluoro-11β-hydroxy-16α-methyl-3-oxo-17α-(2,2,3,3-tertamethylcyclopropylcarbonyl)oxy-androsta-1,4-diene-17β-carboxylate optionally in the form of the racemates, enantiomers or diastereomers thereof and optionally in the form of the salts and derivatives thereof, the solvates and/or hydrates thereof. Any reference to steroids includes a reference to any salts or derivatives, hydrates or solvates thereof which may exist. Examples of possible salts and derivatives of the steroids may be: alkali metal salts, such as for example sodium or potassium salts, sulphobenzoates, phosphates, isonicotinates, acetates, dichloroacetates, propionates, dihydrogen phosphates, palmitates, pivalates or furoates.

PDE4-inhibitors which may be used are preferably compounds selected from among enprofyllin, theophyllin, roflumilast, ariflo (cilomilast), tofimilast, pumafentrin, lirimilast, arofyllin, atizoram, D-4418, Bay-198004, BY343, CP-325.366, D-4396 (Sch-351591), AWD-12-281 (GW-842470), NCS-613, CDP-840, D-4418, PD-168787, T-440, T-2585, V-11294A, C1-1018, CDC-801, CDC-3052, D-22888, YM-58997, Z-15370 and N-(3,5-dichloro-1-oxo-pyridin-4-yl)-4-difluoromethoxy-3-cyclopropylmethoxybenzamide (−)p-[(4aR*,10bS*)-9-ethoxy-1,2,3,4,4a,10b-hexahydro-8-methoxy-2-methylbenzo[s][1,6]naphthyridin-6-yl]-N,N-diisopropylbenzamide (R)-(+)-1-(4-bromobenzyl)-4-[(3-cyclopentyloxy)-4-methoxyphenyl]-2-pyrrolidone 3-(cyclopentyloxy-4-methoxyphenyl)-1-(4-N'-[N-2-cyano-S-methyl-isothioureido]benzyl)-2-pyrrolidone cis[4-cyano-4-(3-cyclopentyloxy-4-methoxyphenyl)cyclohexane-1-carboxylic acid]

2-carbomethoxy-4-cyano-4-(3-cyclopropylmethoxy-4-difluoromethoxy-phenyl)cyclohexan-1-one cis[4-cyano-4-(3-cyclopropylmethoxy-4-difluoromethoxyphenyl)cyclohexan-1-ol]

(R)-(+)-ethyl[4-(3-cyclopentyloxy-4-methoxyphenyl)pyrrolidin-2-ylidene]acetate (S)-(−)-ethyl[4-(3-cyclopentyloxy-4-methoxyphenyl)pyrrolidin-2-ylidene]acetate 9-cyclopentyl-5,6-dihydro-7-ethyl-3-(2-thienyl)-9H-pyrazolo[3,4-c]-1,2,4-triazolo[4,3-a]pyridine 9-cyclopentyl-5,6-dihydro-7-ethyl-3-(tert-butyl)-9H-pyrazolo[3,4-c]-1,2,4-triazolo[4,3-a]pyridine optionally in the form of the racemates, enantiomers or diastereomers thereof and optionally in the form of the pharmacologically acceptable acid addition salts thereof, the solvates and/or hydrates thereof. According to the invention the acid addition salts of the betamimetics are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The LTD4-antagonists used are preferably compounds selected from among montelukast, pranlukast, zafirlukast, MCC-847 (ZD-3523), MN-001, MEN-91507 (LM-1507), VUF-5078, VUF-K-8707, L-733321 and 1-(((R)-3-(2-(6,7-difluoro-2-quinolinyl)ethenyl)phenyl)-3-(2-(2-hydroxy-2-propyl)phenyl)thio)methylcyclopropane-acetic acid, 1-((((1R)-3(3-(2-(2,3-dichlorothieno[3,2-b]pyridin-5-yl)-(E)-ethenyl)phenyl)-3-(2-(1-hydroxy-1-methylethyl)phenyl)propyl)thio)methyl)cyclopropaneacetic acid

[2-[[2-(4-tert-butyl-2-thiazolyl)-5-benzofuranyl]oxymethyl]phenyl]acetic acid optionally in the form of the racemates, enantiomers or diastereomers thereof and optionally in the form of the pharmacologically acceptable acid addition salts, solvates and/or hydrates thereof. According to the invention the acid addition salts of the betamimetics are preferably selected from among the hydrochloride, hydrobromide, hydroiodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate. By salts or derivatives which the LTD4-antagonists may optionally be capable of forming are meant, for example: alkali metal salts, such as for example sodium or potassium salts, alkaline earth metal salts, sulphobenzoates, phosphates, isonicotinates, acetates, propionates, dihydrogen phosphates, palmitates, pivalates or furoates.

EGFR-inhibitors which may be used are preferably compounds selected from among cetuximab, trastuzumab, ABX-EGF, Mab ICR-62 and 4-[(3-chloro-4-fluorophenyl)amino]-6-{[4-(morpholin-4-yl)-1-oxo-2-buten-1-yl]-amino}-7-cyclopropylmethoxy-quinazoline 4-[(3-chloro-4-fluorophenyl)amino]-6-{[4-(N,N-diethylamino)-1-oxo-2-buten-1-yl]amino}-7-cyclopropylmethoxy-quinazoline 4-[(3-chloro-4-fluorophenyl)amino]-6-{[4-(N,N-dimethylamino)-1-oxo-2-buten-1-yl]amino}-7-cyclopropylmethoxy-quinazoline 4-[(R)-(1-phenyl-ethyl)amino]-6-{[4-(morpholin-4-yl)-1-oxo-2-buten-1-yl]-amino}-7-cyclopentyloxy-quinazoline 4-[(3-chloro-4-fluoro-phenyl)amino]-6-{[4-((R)-6-methyl-2-oxo-morpholin-4-yl)-1-oxo-2-buten-1-yl]amino}-7-cyclopropylmethoxy-quinazoline 4-[(3-chloro-4-fluoro-phenyl)amino]-6-{[4-((R)-6-methyl-2-oxo-morpholin-4-yl)-1-oxo-2-buten-1-yl]amino}-7-[(S)-(tetrahydrofuran-3-yl)oxy]-quinazoline 4-[(3-chloro-4-fluoro-phenyl)amino]-6-{[4-((R)-2-methoxymethyl-6-oxo-morpholin-4-yl)-1-oxo-2-buten-1-yl]amino}-7-cyclopropylmethoxy-quinazoline 4-[(3-chloro-4-fluoro-phenyl)amino]-6-[2-((S)-6-methyl-2-oxo-morpholin-4-yl)-ethoxy]-7-methoxy-quinazoline 4-[(3-chloro-4-fluorophenyl)amino]-6-({4-[N-(2-methoxyethyl)-N-methyl-amino]-1-oxo-2-buten-1-yl}amino)-7-cyclopropylmethoxy-quinazoline 4-[(3-chloro-4-fluorophenyl)amino]-6-{[4-(N,N-dimethylamino)-1-oxo-2-buten-1-yl]amino}-7-cyclopentyloxy-quinazoline 4-[(R)-(1-phenyl-ethyl)amino]-6-{[4-(N,N-to-(2-methoxyethyl)-amino)-1-oxo-2-buten-1-yl]amino}-7-cyclopropylmethoxy-quinazoline 4-[(R)-(1-phenyl-ethyl)amino]-6-({4-[N-(2-methoxyethyl)-N-ethyl-amino]-1-oxo-2-buten-1-yl}amino)-7-cyclopropylmethoxy-quinazoline 4-[(R)-(1-phenyl-ethyl)amino]-6-({4-[N-(2-methoxyethyl)-N-methyl-amino]-1-oxo-2-buten-1-yl}amino)-7-cyclopropylmethoxy-quinazoline 4-[(R)-(1-phenyl-ethyl)amino]-6-({4-[N-(tetrahydropyran-4-yl)-N-methyl-amino]-1-oxo-2-buten-1-yl}amino)-7-cyclopropylmethoxy-quinazoline 4-[(3-chloro-4-fluorophenyl)amino]-6-{[4-(N,N-dimethylamino)-1-oxo-2-buten-1-yl]amino}-7-((R)-tetrahydrofuran-3-yloxy)-quinazoline 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline 4-[(3-chloro-4-fluorophenyl)amino]-6-({4-[N-(2-methoxy-ethyl)-N-methyl-amino]-1-oxo-2-buten-1-yl}amino)-7-cyclopentyloxy-quinazoline 4-[(3-chloro-4-fluorophenyl)amino]-6-{[4-(N-cyclopropyl-N-methyl-amino)-1-oxo-2-buten-1-yl]amino}-7-cyclopentyloxy-quinazoline 4-[(3-chloro-4-fluorophenyl)amino]-6-{[4-(N,N-dimethylamino)-1-oxo-2-buten-1-yl]amino}-7-[(R)-(tetrahydrofuran-2-yl)methoxy]-quinazoline 4-[(3-chloro-4-fluorophenyl)amino]-6-{[4-(N,N-dimethylamino)-1-oxo-2-buten-1-yl]amino}-7-[(S)-(tetrahydrofuran-2-yl)methoxy]-quinazoline 4-[(3-ethynyl-phenyl)amino]-6,7-to-(2-methoxy-ethoxy)-quinazoline 4-[(3-chloro-4-fluorophenyl)amino]-7-[3-(morpholin-4-yl)-propyloxy]-6-[(vinyl-carbonyl)amino]-quinazoline 4-[(R)-(1-phenyl-ethyl)amino]-6-(4-hydroxy-phenyl)-7H-pyrrolo[2,3-d]pyrimidine 3-cyano-4-[(3-chloro-4-fluorophenyl)amino]-6-{[4-(N,N-dimethylamino)-1-oxo-2-buten-1-yl]amino}-7-ethoxy-quinoline 4-{[3-chloro-4-(3-fluoro-benzyloxy)-phenyl]amino}-6-(5-{[(2-methanesulphonyl-ethyl)amino]methyl}-furan-2-yl)quinazoline 4-[(R)-(1-phenyl-ethyl)amino]-6-{[4-((R)-6-methyl-2-oxo-morpholin-4-yl)-1-oxo-2-buten-1-yl]amino}-7-methoxy-quinazoline 4-[(3-chloro-4-fluorophenyl)amino]-6-{[4-(morpholin-4-yl)-1-oxo-2-buten-1-yl]-amino}-7-[(tetrahydrofuran-2-yl)methoxy]-quinazoline 4-[(3-chloro-4-fluorophenyl)amino]-6-({4-[N,N-to-(2-methoxy-ethyl)-amino]-1-oxo-2-buten-1-yl}amino)-7-[(tetrahydrofuran-2-yl)methoxy]-quinazoline 4-[(3-ethynyl-phenyl)amino]-6-{[4-(5,5-dimethyl-2-oxo-morpholin-4-yl)-1-oxo-2-buten-1-yl]amino}-quinazoline 4-[(3-chloro-4-fluoro-phenyl)amino]-6-[2-(2,2-dimethyl-6-oxo-morpholin-4-yl)-ethoxy]-7-methoxy-quinazoline 4-[(3-chloro-4-fluoro-phenyl)amino]-6-[2-(2,2-dimethyl-6-oxo-morpholin-4-yl)-ethoxy]-7-[(R)-(tetrahydrofuran-2-yl)methoxy]-quinazoline 4-[(3-chloro-4-fluoro-phenyl)amino]-7-[2-(2,2-dimethyl-6-oxo-morpholin-4-yl)-ethoxy]-6-[(S)-(tetrahydrofuran-2-yl)methoxy]-quinazoline 4-[(3-chloro-4-fluoro-phenyl)amino]-6-{2-[4-(2-oxo-morpholin-4-yl)-piperidin-1-yl]-ethoxy}-7-methoxy-quinazoline 4-[(3-chloro-4-fluoro-phenyl)amino]-6-[1-(tert.-butyloxycarbonyl)-piperidin-4-yloxy]-7-methoxy-quinazoline 4-[(3-chloro-4-fluoro-phenyl)amino]-6-(trans-4-amino-cyclohexan-1-yloxy)-7-methoxy-quinazoline 4-[(3-chloro-4-fluoro-phenyl)amino]-6-(trans-4-methanesulphonylamino-cyclohexan-1-yloxy)-7-methoxy-quinazoline 4-[(3-chloro-4-fluoro-phenyl)amino]-6-(tetrahydropyran-3-yloxy)-7-methoxy-quinazoline 4-[(3-chloro-4-fluoro-phenyl)amino]-6-(1-methyl-piperidin-4-yloxy)-7-methoxy-quinazoline 4-[(3-chloro-4-fluoro-phenyl)amino]-6-{1-[(morpholin-4-yl)carbonyl]-piperidin-4-yloxy}-7-methoxy-quinazoline 4-[(3-chloro-4-fluoro-phenyl)amino]-6-{1-[(methoxymethyl)carbonyl]-piperidin-4-yloxy}-7-methoxy-quinazoline 4-[(3-chloro-4-fluoro-phenyl)amino]-6-(piperidin-3-yloxy)-7-methoxy-quinazoline 4-[(3-chloro-4-fluoro-phenyl)amino]-6-[1-(2-acetylamino-ethyl)-piperidin-4-yloxy]-7-methoxy-quinazoline 4-[(3-chloro-4-fluoro-phenyl)amino]-6-(tetrahydropyran-4-yloxy)-7-ethoxy-quinazoline 4-[(3-chloro-4-fluoro-phenyl)amino]-6-((S)-tetrahydrofuran-3-yloxy)-7-hydroxy-quinazoline 4-[(3-chloro-4-fluoro-phenyl)amino]-6-(tetrahydropyran-4-yloxy)-7-(2-methoxy-ethoxy)-quinazoline 4-[(3-chloro-4-fluoro-phenyl)amino]-6-{trans-4-[(dimethylamino)sulphonylamino]-cyclohexan-1-yloxy}-7-methoxy-quinazoline 4-[(3-chloro-4-fluoro-phenyl)amino]-6-{trans-4-[(morpholin-4-yl)carbonylamino]-cyclohexan-1-yloxy}-7-methoxy-quinazoline 4-[(3-chloro-4-fluoro-phenyl)amino]-6-{trans-4-[(morpholin-4-yl)sulphonylamino]-cyclohexan-1-yloxy}-7-methoxy-quinazoline 4-[(3-chloro-4-fluoro-phenyl)amino]-6-(tetrahydropyran-4-yloxy)-7-(2-acetylamino-ethoxy)-quinazoline 4-[(3-chloro-4-fluoro-phenyl)amino]-6-(tetrahydropyran-4-yloxy)-7-(2-methanesulphonylamino-ethoxy)-quinazoline 4-[(3-chloro-4-fluoro-phenyl)amino]-6-{1-[(piperidin-1-yl)carbonyl]-piperidin-4-yloxy}-7-methoxy-quinazoline 4-[(3-chloro-4-fluoro-phenyl)amino]-6-(1-aminocarbonylmethyl-piperidin-4-yloxy)-7-methoxy-quinazoline 4-[(3-chloro-4-fluoro-phenyl)amino]-6-(cis-4-{N-[(tetrahydropyran-4-yl)carbonyl]-N-methyl-amino}-cyclohexan-1-yloxy)-7-methoxy-quinazoline 4-[(3-chloro-4-fluoro-phenyl)amino]-6-(cis-4-{N-[(morpholin-4-yl)carbonyl]-N-methyl-amino}-cyclohexan-1-yloxy)-7-methoxy-quinazoline 4-[(3-chloro-4-fluoro-phenyl)amino]-6-(cis-4-{N-[(morpholin-4-yl)sulphonyl]-N-methyl-amino}-cyclohexan-1-yloxy)-7-methoxy-quinazoline 4-[(3-chloro-4-fluoro-phenyl)amino]-6-(trans-4-ethanesulphonylamino-cyclohexan-1-yloxy)-7-methoxy-quinazoline 4-[(3-chloro-4-fluoro-phenyl)amino]-6-(1-methanesulphonyl-piperidin-4-yloxy)-7-ethoxy-quinazoline 4-[(3-chloro-4-fluoro-phenyl)amino]-6-(1-methanesulphonyl-piperidin-4-yloxy)-7-(2-methoxy-ethoxy)-quinazoline 4-[(3-chloro-4-fluoro-phenyl)amino]-6-[1-(2-methoxy-acetyl)-piperidin-4-yloxy]-7-(2-methoxy-ethoxy)-quinazoline 4-[(3-chloro-4-fluoro-phenyl)amino]-6-(cis-4-acetylamino-cyclohexan-1-yloxy)-7-methoxy-quinazoline 4-[(3-ethynyl-phenyl)amino]-6-[1-(tert.-butyloxycarbonyl)-piperidin-4-yloxy]-7-methoxy-quinazoline 4-[(3-ethynyl-phenyl)amino]-6-(tetrahydropyran-4-yloxy]-7-methoxy-quinazoline 4-[(3-chloro-4-fluoro-phenyl)amino]-6-(cis-4-{N-[(piperidin-1-yl)carbonyl]-N-methyl-amino}-cyclohexan-1-yloxy)-7-methoxy-quinazoline 4-[(3-chloro-4-fluoro-phenyl)amino]-6-(cis-4-{N-[(4-methyl-piperazin-1-yl)carbonyl]-N-methyl-amino}-cyclohexan-1-yloxy)-7-methoxy-quinazoline 4-[(3-chloro-4-fluoro-phenyl)amino]-6-{cis-4-[(morpholin-4-yl)carbonylamino]-cyclohexan-1-yloxy}-7-methoxy-quinazoline 4-[(3-chloro-4-fluoro-phenyl)amino]-6-{1-[2-(2-oxopyrrolidin-1-yl)ethyl]-piperidin-4-yloxy}-7-methoxy-quinazoline 4-[(3-chloro-4-fluoro-phenyl)amino]-6-{1-[(morpholin-4-yl)carbonyl]-piperidin-4-yloxy}-7-(2-methoxy-ethoxy)-quinazoline 4-[(3-ethynyl-phenyl)amino]-6-(1-acetyl-piperidin-4-yloxy)-7-methoxy-quinazoline 4-[(3-ethynyl-phenyl)amino]-6-(1-methyl-piperidin-4-yloxy)-7-methoxy-quinazoline
4-[(3-ethynyl-phenyl)amino]-6-(1-methanesulphonyl-piperidin-4-yloxy)-7-methoxy-quinazoline
4-[(3-chloro-4-fluoro-phenyl)amino]-6-(1-methyl-piperidin-4-yloxy)-7(2-methoxy-ethoxy)-quinazoline
4-[(3-chloro-4-fluoro-phenyl)amino]-6-(1-isopropyloxycarbonyl-piperidin-4-yloxy)-7-methoxy-quinazoline
4-[(3-chloro-4-fluoro-phenyl)amino]-6-(cis-4-methylamino-cyclohexan-1-yloxy)-7-methoxy-quinazoline
4-[(3-chloro-4-fluoro-phenyl)amino]-6-{cis-4-[N-(2-methoxy-acetyl)-N-methyl-amino]-cyclohexan-1-yloxy}-7-methoxy-quinazoline
4-[(3-ethynyl-phenyl)amino]-6-(piperidin-4-yloxy)-7-methoxy-quinazoline
4-[(3-ethynyl-phenyl)amino]-6-[1-(2-methoxy-acetyl)-piperidin-4-yloxy]-7-methoxy-quinazoline
4-[(3-ethynyl-phenyl)amino]-6-{1-[(morpholin-4-yl)carbonyl]-piperidin-4-yloxy}-7-methoxy-quinazoline
4-[(3-chloro-4-fluoro-phenyl)amino]-6-{1-[(cis-2,6-dimethyl-morpholin-4-yl)carbonyl]-piperidin-4-yloxy}-7-methoxy-quinazoline
4-[(3-chloro-4-fluoro-phenyl)amino]-6-{1-[(2-methyl-morpholin-4-yl)carbonyl]-piperidin-4-yloxy}-7-methoxy-quinazoline
4-[(3-chloro-4-fluoro-phenyl)amino]-6-{1-[(S,S)-(2-oxa-5-aza-bicyclo[2,2,1]hept-5-yl)carbonyl]-piperidin-4-yloxy}-7-methoxy-quinazoline
4-[(3-chloro-4-fluoro-phenyl)amino]-6-{1-[(N-methyl-N-2-methoxyethyl-amino)carbonyl]-piperidin-4-yloxy}-7-methoxy-quinazoline
4-[(3-chloro-4-fluoro-phenyl)amino]-6-(1-ethyl-piperidin-4-yloxy)-7-methoxy-quinazoline
4-[(3-chloro-4-fluoro-phenyl)amino]-6-{1-[(2-methoxyethyl)carbonyl]-piperidin-4-yloxy}-7-methoxy-quinazoline
4-[(3-chloro-4-fluoro-phenyl)amino]-6-{1-[(3-methoxypropyl-amino)-carbonyl]-piperidin-4-yloxy}-7-methoxy-quinazoline
4-[(3-chloro-4-fluoro-phenyl)amino]-6-[cis-4-(N-methanesulphonyl-N-methyl-amino)-cyclohexan-1-yloxy]-7-methoxy-quinazoline
4-[(3-chloro-4-fluoro-phenyl)amino]-6-[cis-4-(N-acetyl-N-methyl-amino)-cyclohexan-1-yloxy]-7-methoxy-quinazoline
4-[(3-chloro-4-fluoro-phenyl)amino]-6-(trans-4-methylamino-cyclohexan-1-yloxy)-7-methoxy-quinazoline
4-[(3-chloro-4-fluoro-phenyl)amino]-6-[trans-4-(N-methanesulphonyl-N-methyl-amino)-cyclohexan-1-yloxy]-7-methoxy-quinazoline
4-[(3-chloro-4-fluoro-phenyl)amino]-6-(trans-4-dimethylamino-cyclohexan-1-yloxy)-7-methoxy-quinazoline
4-[(3-chloro-4-fluoro-phenyl)amino]-6-(trans-4-{N-[(morpholin-4-yl)carbonyl]-N-methyl-amino}-cyclohexan-1-yloxy)-7-methoxy-quinazoline
4-[(3-chloro-4-fluoro-phenyl)amino]-6-[2-(2,2-dimethyl-6-oxo-morpholin-4-yl)-ethoxy]-7-[(S)-(tetrahydrofuran-2-yl)methoxy]-quinazoline
4-[(3-chloro-4-fluoro-phenyl)amino]-6-(1-methanesulphonyl-piperidin-4-yloxy)-7-methoxy-quinazoline
4-[(3-chloro-4-fluoro-phenyl)amino]-6-(1-cyano-piperidin-4-yloxy)-7-methoxy-quinazoline
optionally in the form of the racemates, enantiomers, diastereomers thereof and optionally in the form of the pharmacologically acceptable acid addition salts, solvates or hydrates thereof. According to the invention the acid addition salts of the betamimetics are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The dopamine agonists used are preferably compounds selected from among bromocriptin, cabergoline, alpha-dihydroergocryptine, lisuride, pergolide, pramipexol, roxindol, ropinirol, talipexol, tergurid and viozan, optionally in the form of the racemates, enantiomers, diastereomers thereof and optionally in the form of the pharmacologically acceptable acid addition salts, solvates or hydrates thereof. According to the invention the acid addition salts of the betamimetics are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydrooxalate, hydrosuccinate, hydrobenzoate and hydro-p-toluenesulphonate.

H1-Antihistamines which may be used are preferably compounds selected from among epinastine, cetirizine, azelastine, fexofenadine, levocabastine, loratadine, mizolastine, ketotifen, emedastine, dimetindene, clemastine, bamipine, cexchlorpheniramine, pheniramine, doxylamine, chlorphenoxamine, dimenhydrinate, diphenhydramine, promethazine, ebastine, desloratidine and meclozine, optionally in the form of the racemates, enantiomers, diastereomers thereof and optionally in the form of the pharmacologically acceptable acid addition salts, solvates or hydrates thereof. According to the invention the acid addition salts of the betamimetics are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

It is also possible to use inhalable macromolecules as disclosed in EP 1 003 478 A1 or CA 2297174 A1.

In addition, the compound may come from the group of ergot alkaloid derivatives, the triptans, the CGRP-inhibitors, the phosphodiesterase-V inhibitors, optionally in the form of the racemates, enantiomers or diastereomers thereof, optionally in the form of the pharmacologically acceptable acid addition salts, the solvates and/or hydrates thereof.

Examples of ergot alkaloid derivatives are dihydroergotamine and ergotamine.

LIST OF REFERENCE NUMERALS 1 inhaler
2 formulation
3 carrier
4 receptacle
4a cover
5 air current
6 element
7 chamber
8 supply channel
9 mouthpiece
10 pump
11 section
12 cut
13 chamber
14 guide
15 connecting section
16 delivery channel
17 delivery channel 18 inlet channel
19 inlet valve
20 pump chamber
20a wall portion
20b wall portion
20c wall portion
21 outlet valve
22 double arrow

The invention claimed is:

1. An inhaler for inhaling a formulation, comprising:
a housing having an interior chamber, an air inlet into the chamber, and an outlet from the chamber; and
a carrier disposed within the chamber and operating to supply the formulation, such that a first end of the carrier is free and an opposite second end is fixed in position during inhalation, thereby defining a longitudinal direction along the carrier from the first end to the second end,
wherein the inlet and chamber are operable to permit an air current to flow in the longitudinal direction between the first and second ends of the carrier to set the carrier vibrating during inhalation such that the formulation is disbursed from the carrier, and
wherein the carrier has at least one receptacle containing the formulation and a cover that is opened only partially or by means of a few holes, in order to deliver the formulation, only immediately prior to or for the purpose of dispensing the formulation.

2. The inhaler according to claim 1, wherein:
the carrier is at least one of: flexible, flat, in the form of a ribbon, a strip, a thread, a blister and a foil;
the chamber and carrier are arranged such that the air current flows on a first side of the carrier remote from the formulation, curls over the first end of the carrier, and then flows on a second, opposite side of the carrier supplying the formulation; and
the carrier vibrates at right angles to the longitudinal direction.

3. Inhaler according to claim 1, further comprising a receptacle containing a single dose of the formulation is arranged on the carrier such that the air current flows in the longitudinal direction from the first end of the carrier and across the receptacle to disburse the formulation from the receptacle, into the air current, and through the outlet.

4. The inhaler according to claim 1, wherein the air current is generated or initiated by inhaling.

5. The inhaler according to claim 1, wherein the carrier is of elongate construction and contains a plurality of doses of the formulation which can be expelled one after another.

6. The inhaler according to claim 5, wherein:
the carrier includes a plurality of slits initiating at the first end and extending toward, but not reaching the second end, the slits being spaced apart from one another to define respective carrier portions between respective pairs of slits, such that the first ends of each respective carrier portion is separately movable;
a respective one of the plurality of doses of the formulation is disposed on each carrier portion.

7. The inhaler according to claim 1, wherein the carrier is moved or conveyed stepwise into the chamber.

8. The inhaler according to claim 1, further comprising a pump for producing the air current.

9. The inhaler according to claim 1, wherein the air current acts as a conveying medium for expelling the formulation.

10. The inhaler according to claim 1, wherein the inhaler is constructed so that independently of the air current another conveying medium serves to expel the formulation.

11. The inhaler according to claim 1, wherein the formulation is powdered.

12. The inhaler according to claim 1, wherein the inhaler is designed to be portable and/or operates purely mechanically.

13. An inhaler for inhaling a formulation, comprising:
a housing having an interior chamber, an air inlet into the chamber, and an outlet from the chamber;
at least one of a carrier and a delivery channel disposed within the chamber and operating to supply the formulation; and
an object that is disposed and movable within the chamber, but not directly or indirectly connected to the housing,
wherein the inlet and chamber are operable to permit an air current to flow into the chamber and set the object vibrating during inhalation such that the object strikes the at least one carrier and delivery channel and causes the formulation to be disbursed from the at least one carrier and delivery channel.

14. The inhaler according to claim 13, wherein the object is spherical or cylindrical in construction.

15. The inhaler according to claim 14, wherein the air current flows onto the object in a direction of back-and-forth movement of the object.

16. The inhaler according to claim 13 wherein the object strikes the carrier at right angles to the longitudinal direction on a side of the carrier remote from the formulation.

17. A method of delivering and atomising a formulation, comprising:
providing a flexible, flat carrier in the form of a at least one of a strip and blister, the carrier including a receptacle within which the formulation is disposed, and a cover sealing the receptacle;
at least partially removing the cover to expose the formulation through a relatively small opening; and
introducing an air current for one of vibrating the carrier and vibrating an object that strikes the carrier, such that the formulation is disbursed from the receptacle through the opening.

18. An inhaler for inhaling a formulation, comprising:
a housing having an interior chamber, an air inlet into the chamber, and an outlet from the chamber; and
a carrier disposed within the chamber and operating to supply the formulation, such that a first end of the carrier is free and an opposite second end is fixed in position during inhalation, thereby defining a longitudinal direction along the carrier from the first end to the second end, wherein:
the inlet and chamber are operable to permit an air current to flow in the longitudinal direction between the first and second ends of the carrier to set the carrier vibrating during inhalation such that the formulation is disbursed from the carrier, and
the carrier is at least one of: flexible, flat, in the form of a ribbon, a strip, a thread, a blister and a foil;
the chamber and carrier are arranged such that the air current flows on a first side of the carrier remote from the formulation, curls over the first end of the carrier, and then flows on a second, opposite side of the carrier supplying the formulation; and
the carrier vibrates at right angles to the longitudinal direction.

19. An inhaler for inhaling a formulation, comprising:
a delivery channel having an inlet, an outlet, and a supply of the formulation, whereby the delivery channel is flexible along at least a portion thereof;
an object that is disposed and movable relative to the delivery channel;

wherein the object vibrates in response to a flow of air during inhalation such that the object strikes the flexible portion of the delivery channel and causes the formulation to be disbursed from the delivery channel.

20. An inhaler for inhaling a formulation, comprising:
a housing having an interior chamber, an air inlet into the chamber, and an outlet from the chamber; and
a carrier disposed within the chamber and operating to supply the formulation, such that a first end of the carrier is free and an opposite second end is fixed in position during inhalation, thereby defining a longitudinal direction along the carrier from the first end to the second end,
wherein the inlet and chamber are operable to permit an air current to flow in the longitudinal direction between the first and second ends of the carrier to set the carrier vibrating during inhalation such that the formulation is disbursed from the carrier,
wherein the carrier includes a plurality of slits initiating at the first end and extending toward, but not reaching the second end, the slits being spaced apart from one another to define respective carrier portions between respective pairs of slits, such that the first ends of each respective carrier portion is separately movable, and
wherein a respective one of the plurality of doses of the formulation is disposed on each carrier portion.

* * * * *

UNITED STATES PATENT AND TRADEMARK OFFICE
CERTIFICATE OF CORRECTION

PATENT NO.         : 8,528,548 B2                                    Page 1 of 1
APPLICATION NO.    : 12/441177
DATED              : September 10, 2013
INVENTOR(S)        : Heinrich Kladders It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1200 days.

Signed and Sealed this

Fifteenth Day of September, 2015

Michelle K. Lee
*Director of the United States Patent and Trademark Office*